United States Patent
Lang et al.

(10) Patent No.: US 7,759,509 B2
(45) Date of Patent: Jul. 20, 2010

(54) HIGHLY REACTIVE ZINC FORM, METHOD FOR THE PRODUCTION THEREOF, AND USE OF THE SAME

(75) Inventors: Sebastian Lang, Frankfurt am Main (DE); Alexander Murso, Frankfurt am Main (DE); Ulrich Wietelmann, Friedrichsdorf (DE)

(73) Assignee: Chemetall GmbH, Frankfurt am Main (DE)

( * ) Notice: Subject to any disclaimer, the term of this patent is extended or adjusted under 35 U.S.C. 154(b) by 38 days.

(21) Appl. No.: 11/990,424

(22) PCT Filed: Aug. 21, 2006

(86) PCT No.: PCT/EP2006/065506

§ 371 (c)(1),
(2), (4) Date: Jun. 5, 2008

(87) PCT Pub. No.: WO2007/020298

PCT Pub. Date: Feb. 22, 2007

(65) Prior Publication Data

US 2009/0118529 A1    May 7, 2009

(30) Foreign Application Priority Data

Aug. 19, 2005  (DE)  ........................ 10 2005 039 628
Aug. 25, 2005  (DE)  ........................ 10 2005 040 391

(51) Int. Cl.
*C07F 3/06*  (2006.01)
*C01G 9/00*  (2006.01)

(52) U.S. Cl. ....................... 556/121; 423/101

(58) Field of Classification Search ................ 556/121; 423/101

See application file for complete search history.

(56) References Cited

U.S. PATENT DOCUMENTS

| 5,124,082 | A | * | 6/1992 | Takahashi et al. ........... 554/130 |
| 5,756,653 | A | | 5/1998 | Rieke |
| 5,964,919 | A | | 10/1999 | Rieke |
| 2002/0014135 | A1 | | 2/2002 | Frommeyer et al. |
| 2004/0236155 | A1 | | 11/2004 | Perichon |

FOREIGN PATENT DOCUMENTS

| DE | 100 24 776 C1 | 9/2001 |
| EP | 0 252 766 A1 | 1/1988 |

OTHER PUBLICATIONS

Takai, et al "A Dramatic Effect of a Catalytic Amount of Formation of Alkyzinc compounds from Iodoalkanes. Reactivity of Zinc metal: Activation and Deactivation", Journal of Organic Chemistry. pp. 2671-2673.

Joubert, et al., "Preparation of New Classes of Aliphatic, Allytic, and Benzylic Zinc and Copper Reagents, by the Insertion of Zinc Dust into organic halides, Phosphates, and Sulfonates", Journal of Organic Chemistry. pp. 5425-5431.

* cited by examiner

*Primary Examiner*—Porfirio Nazario Gonzalez
(74) *Attorney, Agent, or Firm*—Fulbright & Jaworski L.L.P.

(57) ABSTRACT

The invention relates to a highly reactive zinc form, to a method for the production thereof, and to the use of said highly reactive zinc form in synthetic chemistry.

26 Claims, No Drawings

HIGHLY REACTIVE ZINC FORM, METHOD FOR THE PRODUCTION THEREOF, AND USE OF THE SAME

RELATED APPLICATIONS

This application is a §371 of PCT/EP2006/065506 filed Aug. 21, 2006, which claims priority from German Patent Application No: 10 2005 039 628.3 filed Aug. 19, 2005 and German Patent Application No: 10 2005 040 391.3 filed Aug. 25, 2005.

The invention provides a highly reactive form of zinc, a process for its preparation and the use of the highly reactive form of zinc in synthetic chemistry.

Organozinc compounds have a variety of applications in organic synthesis. The best-known examples of such applications are the Reformatsky, Simmons-Smith and Negishi reactions. Organozinc compounds (zinc organyls) facilitate the preparation of highly functionalized substances which are important starting materials for the preparation of pharmaceuticals, natural substance derivatives, polymer materials, agrochemicals, specialities and catalysts. In contrast to other organometallic compounds, zinc organyls tolerate a large number of functional groups, making zinc organyls a unique class of compounds and distinguishing them from other organometallic reagents. Another difference from other organometallic compounds is the fact that, in the presence of suitable catalysts, organozinc compounds often react stereoselectively and regioselectively with organic substrates (P. Knochel, P. Jones in Organozinc Reagents (Editors: L. M. Harwood, C. J. Moody), Oxford; University Press Inc., New York, 1999, and references contained therein; A. Fürstner, Active Metals, VCH, Weinheim, N.Y., 1996, and references contained therein).

The processes described below, inter alia, have been disclosed for the preparation of organozinc compounds:

1. Preparation of Organozinc Compounds Via Transmetallation

Transmetallations of zinc halides with organolithium, organomagnesium or organoaluminium compounds produce organozinc compounds. However, the main problem with this process is the fact that the presence of many desirable functional groups, e.g. esters, ketones, nitrites, etc., in the organic fragment is excluded by the incompatibility of many of these groups with such organometallic compounds (Scheme 1).

Scheme 1:
Preparation of organozinc compounds via transmetallation:

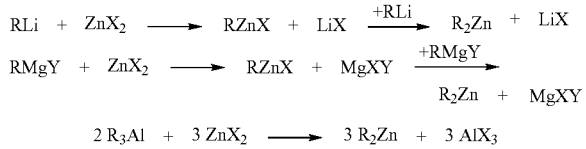

X, Y = halogen; R = organic radical

2. Comproportionation Reaction for the Preparation of Organozinc Compounds

A comproportionation reaction of a diorganozinc compound with a zinc salt also produces organozinc compounds. However, the use of this process is limited by the availability of diorganozinc species and the possible ways of preparing them (Scheme 2).

Scheme 2:
Comproportionation reaction for the preparation of organozinc compounds:

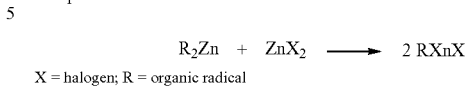

X = halogen; R = organic radical

3. Iodine/Zinc Exchange Reaction

Organozinc compounds can also be prepared via iodine/zinc or boron/zinc exchange reactions. Iodine/zinc exchange reactions facilitate the conversion of alkyl iodides to the corresponding organozinc compounds by treatment with dialkylzinc reagents. However, this process is limited to alkyl iodides, some of which are commercially unavailable, often unstable and also expensive, so it is not generally applicable (Scheme 3).

Scheme 3:
Iodine/zinc exchange reaction:

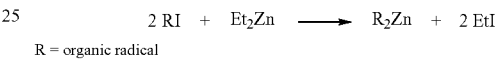

R = organic radical

4. Boron/Zinc Exchange Reactions

Hydroboration reactions of alkenes with diethylborane, followed by reaction with a dialkylzinc compound, likewise yield the corresponding organozinc compounds. A disadvantage of this process is the essential hydro-boration reaction, which represents an additional synthetic step in the preparation of organozinc compounds. Moreover, because it is restricted to alkenes, the hydroboration reaction is limited to the preparation of alkylzinc compounds (Scheme 4).

Scheme 4:
Boron/zinc exchange reactions:

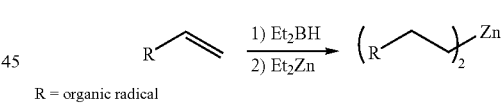

R = organic radical

Both the iodine/zinc and the boron/zinc exchange reactions additionally require a dialkylzinc compound in order to prepare another organozinc compound.

5. Thermal Disproportionation of an Organozinc Halide

Another process for the preparation of diorganozinc compounds is the thermally induced disproportionation of organozinc halides. However, this process is dependent on the availability of an appropriate organozinc halide (Scheme 5).

Scheme 5:
Thermal disproportionation of an organozinc halide:

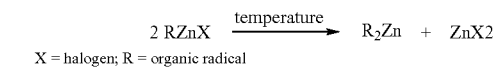

X = halogen; R = organic radical

6. Oxidative Addition for the Preparation of Organozinc Compounds

Theoretically the simplest process for the preparation of organozinc compounds is the oxidative addition of zinc onto organic halides. The synthesis does not require organozinc compounds or any other organometallic compounds (Scheme 6) (P. Knochel, P. Jones in Organozinc Reagents (Editors: L. M. Harwood, C. J. Moody), Oxford; University Press Inc., New York, 1999, and references contained therein; A. Fürstner, Active Metals, VCH, Weinheim, N.Y., 1996, and references contained therein).

Scheme 6:
Oxidative addition for the preparation of organozinc compounds:

X = halogen; R = organic radical

A problem with this process, however, is the zinc used, which in this case is "technical-grade" zinc metal. Independently of particle size or surface structure, technical-grade zinc metal is covered with a metal-passivating layer which deactivates the metal in respect of an oxidative addition and particularly in respect of an oxidative addition onto organic halides.

Because of the passivating layer, an oxidative addition of technical-grade zinc onto organic halides is usually only possible if the metal is first treated by suitable processes and, in addition, only with specially selected, highly reactive organic bromides, e.g. allyl bromide, or iodides.

Much effort has therefore been devoted to activating the poorly reactive zinc in order to accelerate an oxidative addition onto organic iodides and to enable an oxidative addition onto bromides (P. Knochel, P. Jones in Organozinc Reagents (Editors: L. M. Harwood, C. J. Moody), Oxford; University Press Inc., New York, 1999, and references contained therein; A. Fürstner, Active Metals, VCH, Weinheim, N.Y., 1996, and references contained therein; E. Erdik, Tetrahedron 1987, 43, 2203).

By way of simplification, the expression "forms of zinc" will be used hereafter when the zinc metal is in activated form.

Various washing processes are thus described for removing the passivating surface from technical-grade zinc. One possibility consists in washing the metal with dilute aqueous hydrochloric acid solution, with water and finally with acetone and ether. Another process consists in washing with dilute aqueous sodium hydroxide solution, then with dilute acetic acid and water and finally with acetone and ether. The passivating surface can also be removed by washing the zinc metal with saturated ammonium chloride solution, then decanting the washing solution and rinsing the residue with water and finally with ethanol, ether and dimethylformamide. In these washing processes, the form of zinc obtained has to be dried under vacuum before use.

These processes for activating zinc metal are laborious because of the many different washing steps and final drying of the activated zinc, and moreover produce forms of zinc which are only of limited use for oxidative additions, e.g. in reactions with strongly activated iodoalkyl esters, α-bromo esters, α-bromo nitrites or benzyl halides, or in Reformatsky reactions. In addition, the efficiency of these activation methods is strongly dependent on the type of zinc metal used, i.e. on the size and structure of its surface. According to the reactivity of the organic halide, the use of either electrolytically produced zinc turnings, zinc dust or zinc wool produces the desired products in satisfactory yields. The use of zinc dust additionally has the disadvantage of being difficult to separate from the reaction solution.

The use of forms of zinc such as so-called "zinc-copper couples" or "zinc-silver couples" is limited to Simmons-Smith reactions and reactions with strongly activated alkyl iodides. The conventional "zinc-copper couple" is obtained by the treatment of zinc metal with hydrochloric acid and water as referred to above, followed by the addition of copper sulfate solution and repeated washing of the treated zinc metal with water and ether. A zinc-silver couple is prepared by using silver acetate in acetic acid instead of copper sulfate. These forms of zinc have to be dried under vacuum before being used in synthesis. The disadvantage of using conventionally prepared zinc-copper couples or zinc-silver couples is thus not only their limited possible uses and the variable quality of the activation due to the complex preparation, but also their laborious preparation, the drying and the disposal of contaminated washing solutions. Another "zinc-copper couple" is obtained by refluxing a mixture of zinc metal and copper halides in ethers. The copper halide used can also be replaced by powdered copper metal, but the use of copper gives poorer yields. This form of zinc is found to be more reactive than the conventionally prepared zinc-copper couple in Simmons-Smith reactions, but again is limited only to Simmons-Smith reactions and reactions with strongly activated alkyl iodides (E. Erdik, Tetrahedron 1987, 43, 2203; R. J. Rawson et al., J. Org. Chem. 1970, 35, 2057).

The use of alanes, or alkali-metal or alkaline-earth metal aluminium hydrides, in cyclopropanation reactions Simmons-Smith reactions) is disclosed in U.S. Pat. No. 4,472,313. This process makes it possible to carry out Simmons-Smith reactions without the laborious preparation of a zinc-copper couple, but once again it is restricted only to Simmons-Smith reactions.

Other processes for the preparation of activated zinc are the etching of zinc metal with iodine, alkylmagnesium halides, trimethylsilyl chloride, dialkylaluminium chloride or 1,2-dibromoethane and trimethylsilyl chloride. These reagents produce forms of zinc which only allow oxidative additions of zinc onto alkyl iodides and strongly activated alkyl bromides, e.g. α-bromo esters, and which moreover can only be used in Reformatsky and Simmons-Smith reactions.

The treatment of metallic zinc with ultrasound also produces activated zinc. If the ultrasound treatment is carried out simultaneously with one of the etching processes referred to above, this form of zinc is more reactive than without ultrasound treatment, but is nevertheless subject to the same applicability limits as regards reaction with organic halides, so this form of zinc can also be used only for insertions of zinc into strongly activated organic bromides or into iodides, or in Reformatsky reactions.

Thus, despite these numerous different processes for the preparation of activated zinc, an oxidative addition is only possible with reactive organic halides, e.g. iodides, α-halogeno esters or α,β-unsaturated bromides. The majority of alkyl bromides or chlorides, vinyl or allyl halides and aryl halides react only very slowly, if at all, with the forms of zinc described above.

Those skilled in the art are also familiar with a number of processes for the preparation of activated zinc from the patent literature.

Thus WO 03/004504 A1 discloses the synthesis of arylzinc halides using technical-grade zinc metal, a cobalt-containing catalyst, a zinc salt, an organic acid and another aryl halide present in catalytic amounts. One disadvantage of this process is the use of an additional halogenated aromatic compound, e.g. bromobenzene. The presence of bromobenzene as an additive in the reaction mixture results in the formation of benzene, which is highly toxic and carcinogenic. The use of catalytic amounts of other aryl halides as an additive likewise results in the formation of unwanted by-products. If allyl chloride is used instead of catalytic amounts of an aryl halide, arylzinc halides can still be prepared, but the product solution contains impurities attributable to the presence of allyl chloride (C. Gosmini, J. Am. Chem. Soc. 2003, 125, 3867; C. Gosmini, Tetrahedron Lett. 2003, 44, 6417). Another disadvantage is the presence of an organic acid, because the product formed is not pure and the acid, or its derivatives formed after the reaction, cannot easily be separated from the desired main product. Moreover, this process can only be carried out in selected solvents, e.g. acetonitrile. In addition, this method can only be applied to $sp^2$-hybridized carbon atoms.

SU-A-1775403 discloses the synthesis of high-purity diethylzinc via a thermal disproportionation of ethylzinc bromide. Ethylzinc bromide is prepared by reacting ethyl bromide with zinc powder in the presence of a system for catalysing the reaction. The catalytic systems used are alkylzinc halides or dialkylzinc compounds in combination with zinc hydroxide and/or transition-metal compounds. Although this process gives good yields of diethylzinc, markedly lower yields are found in the preparation of secondary and longer-chain dialkylzinc compounds. The application of this process to the preparation of secondary and longer-chain dialkylzinc compounds additionally requires long reaction times (I. V. Eremeev, Rus. J. Appl. Chem. 2001, 74, 1410). The low yields also indicate that the longer-chain dialkylzinc compounds are either contaminated or contain unreacted alkyl halide. Technically laborious purification steps are thus necessary for obtaining pure product solutions.

DE-C-100 24 776 and EP-A-1 031 634 disclose another process for the preparation of activated zinc and describe the treatment of molten zinc with metal hydrides. The resulting form of zinc has proved suitable for Simmons-Smith reactions. However, the process necessitates the melting of zinc metal and subsequent grinding, which is technically laborious, time-consuming and expensive.

A form of zinc that is generally applicable to oxidative addition reactions onto organic halides (referred to here as "special zinc") has to be prepared by laborious and expensive processes, which are described below. Special zinc is an activated zinc which does not have to be activated by the above-described processes of the prior art for the synthesis of organozinc compounds. Special zinc does not have a layer that passivates the zinc metal. One of these processes for the preparation of this form of zinc consists of metal/solvent co-condensation, where technical-grade zinc metal is vaporized under reduced pressure in a solvent atmosphere, conventionally by means of an electrical resistive heating source, and condensed onto surfaces cooled by liquid nitrogen or helium. Ultrafine, nanoscale metal atom clusters are formed as a slurry in the solvent. Although this process produces a very reactive form of zinc, it is technically very laborious because of the extremely high temperatures required to vaporize the metal, the handling of very cold liquefied gases for condensing the metal, and the need to operate under vacuum, so it is extremely expensive and only suitable for the preparation of relatively small amounts of activated zinc (A. Fürstner, Active Metals, VCH, Weinheim, N.Y., 1996, and references contained therein).

Electrochemical methods of synthesizing arylzinc or vinylzinc halides in a sacrificial anode process or in the presence of a catalyst, where special zinc is prepared in situ, are also known, but they suffer from the disadvantages generally associated with electrochemical processes. Such processes are thus relatively expensive and demand a large technical outlay. Larger amounts of special zinc cannot easily be prepared by these processes. Also, such processes are limited to the preparation of arylzinc and vinylzinc halides (Editors: L. M. Harwood, C. J. Moody), Oxford; University Press Inc., New York, 1999, and references contained therein; WO 01/02625 A1; H. Fillon et al., Tetrahedron Lett. 2001, 42, 3843; C. Gosmini et al., J. Org. Chem. 2000, 65, 6024).

Another process for the preparation of special zinc is described by Rieke (P. Knochel, P. Jones in Organozinc Reagents (Editors: L. M. Harwood, C. J. Moody), Oxford; University Press Inc., New York, 1999, and references contained therein; A. Fürstner, Active Metals, VCH, Weinheim, N.Y., 1996, and references contained therein). This form of zinc (also called Rieke® zinc hereafter) is produced by reducing a zinc salt—e.g. $ZnCl_2$ or $Zn(CN)_2$—with an alkali metal—preferably Li—in the presence of stoichiometric or catalytic amounts of an electron carrier (e.g. naphthalene) and is obtained as a finely divided, highly reactive powder (Scheme 7).

Scheme 7:
Preparation of Rieke® zinc

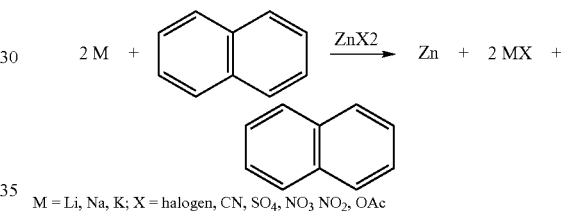

M = Li, Na, K; X = halogen, CN, $SO_4$, $NO_3$ $NO_2$, OAc

Typical particle sizes of the forms of zinc prepared by the Rieke® process (Rieke® zinc) are between one and two μm down to the nanometre range. The size of the particles formed is very dependent on the type of Rieke® zinc preparation, e.g. on the rate of addition of the reagents or the stirrer speed and the alkali metals and zinc salts used. If the zinc powder is not obtained in finely divided form, it has a lower reactivity. As a consequence of its preparation, Rieke® zinc is contaminated with the alkali-metal salt used for the reduction, and with other accompanying substances formed by the redox processes that take place.

In the Rieke® process about two mol of alkali metal are oxidized per mol of zinc metal produced (U.S. Pat. No. 5,964, 919; WO 93/15086 A1). The finely divided metal powder is obtained together with large amounts of alkali-metal salt. Therefore, if Rieke® zinc is used in oxidative addition reactions with the intention of obtaining pure product, the zinc prepared by the Rieke® process must first be purified. The alkali-metal salts cannot easily be completely separated from the zinc metal by repeated washing with suitable organic solvents. Moreover, the small particle sizes of Rieke® zinc demand a purification of the metal that is technically extremely laborious, because centrifugation and filtration are only of limited suitability for the work-up. In addition, the type of anion in the alkali-metal salt strongly influences the reactivity of Rieke® zinc in oxidative addition reactions, the presence of alkali-metal salts being essential for reactions with less reactive substrates. Thus contamination of the product solution with alkali-metal salts has to be accepted in some cases. To illustrate the amounts of alkali-metal salt formed in the preparation of Rieke® zinc, Table 1 below shows the amounts of alkali-metal salt when using lithium, sodium and potassium to reduce zinc chloride. The calculations are based on 100% conversion and the preparation of one kilogram of Rieke® zinc.

TABLE 1

Amounts of alkali-metal salt in the preparation of 1 kg (15.3 mol) of Rieke ® zinc from zinc chloride:

| metal | amount of substance used [mol] | salt formed | molecular weight of the salt [g/mol] | amount of salt obtained per kg of Rieke ® zinc [kg] |
| --- | --- | --- | --- | --- |
| Li | 30.6 | LiCl | 42.39 | 1.3 |
| Na | 30.6 | NaCl | 58.44 | 1.8 |
| K | 30.6 | KCl | 74.55 | 2.3 |

The disadvantages of all the above-described methods of preparing activated zinc are either that they are relatively laborious and expensive or of only limited applicability and/or efficiency, and/or that they give non-reproducible or poor yields. The technical problem of an efficient and economic preparation of organozinc compounds via an oxidative addition onto organic halogen compounds that does not suffer from the stated disadvantages thus remains unsolved.

The object of the present invention is therefore to overcome the disadvantages of the prior art.

In particular, one object of the present invention is to provide a highly reactive zinc metal.

Another object of the invention is to provide a highly reactive zinc metal which has a similar reactivity to that of the finely divided, special zinc prepared by the Rieke® process.

Another object of the invention is to provide a highly reactive zinc metal which also inserts into non-activated carbon-halogen bonds.

Another object of the invention is to provide a highly reactive zinc metal which does not contain the alkali-metal impurities present in the finely divided, special zinc prepared by the Rieke® process.

Another object of the invention is to provide a highly reactive zinc metal which has a better filterability than the finely divided, special zinc prepared by the Rieke® process.

Another object of the invention is to provide a process for the preparation of the highly reactive zinc metal.

Another object of the invention is to provide a process for the preparation of the highly reactive zinc metal which makes it possible to prepare organozinc compounds from organic halides with high yields and short reaction times.

Another object of the invention is to provide a process for the preparation of the highly reactive zinc metal which avoids high temperatures and exotic, corrosive reaction media like molten salts, or multistage processes, e.g. solvent changes, washing and drying steps or electrolysis.

Another object of the invention is to provide a process for the preparation of the highly reactive zinc metal which is less expensive than the Rieke® process.

Surprisingly, the object is achieved by the features of the main claim. Preferred embodiments can be found in the subordinate claims.

In particular, the object is achieved, surprisingly, by the form of zinc according to the invention. This form of zinc contains 50 to 99.99 wt. %, preferably 80 to 99.99 wt. %, of highly reactive zinc metal. For the purposes of the invention, "highly reactive zinc metal" is a form of zinc which is more reactive than untreated technical-grade zinc metal or technical-grade zinc metal activated according to the prior art. The form of zinc according to the invention has a comparable reactivity to that of the finely divided, special form of zinc prepared by the Rieke® process. However, the form of zinc according to the invention has a coarser particle size than the finely divided, special form of zinc prepared by the Rieke® process. In particular, the form of zinc according to the invention has a particle size above 2 μm, preferably of 10 to 500 μm and particularly preferably of 50 to 350 μm. Preferably, the form of zinc according to the invention is not contaminated with alkali-metal halides, cyanides, sulfates, nitrates, nitrites or acetates and/or with other alkali-metal salts used according to the prior art for the preparation of Rieke® zinc.

The chosen criterion for the reactivity of the form of zinc according to the invention compared with a form of zinc prepared by the Rieke® process was the rate and yield of insertion into organic bromine compounds. It is known from the prior art that untreated technical-grade zinc metal or technical-grade zinc metal activated in conventional manner only inserts into organic iodine compounds or particularly reactive bromine compounds, e.g. α,β-unsaturated organic bromides. In oxidative addition reactions according to Scheme 6:

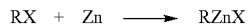

X = halogen; R = organic radical tertiary organic halides react faster than secondary organic halides, which in turn react faster than primary organic halides. Functionalized tertiary, secondary or primary halides normally react faster than their non-functionalized analogues (P. Knochel, P. Jones in Organozinc Reagents (Editors: L. M. Harwood, C. J. Moody), Oxford; University Press Inc., New York, 1999, and references contained therein; A. Fürstner, Active Metals, VCH, Weinheim, N.Y., 1996, and references contained therein; R. D. Rieke et al., J. Chem. Soc. Chem. Commun. 1973, 269; R. D. Rieke et al., Tetrahedron 1997, 1925; R. D. Rieke et al., J. Org. Chem. 1996, 61, 2726; L. Zhu et al., J. Org. Chem. 1991, 56, 1445). Accordingly, high yields and short reaction times when using the form of zinc according to the invention in reactions with n-butyl bromide (known to be slow-reacting) as a primary organic halide verify the general applicability of the form of zinc according to the invention in organometallic synthesis.

It has also been found, surprisingly, that the form of zinc according to the invention makes it possible also to insert zinc into non-activated carbon-halogen bonds.

The form of zinc according to the invention is characterized in particular in that, with n-butyl bromide in oxidative addition reactions according to Scheme 6, it gives yields of n-butylzinc bromide of over 50% within a period of five hours at temperatures below 150° C.

The form of zinc according to the invention makes it possible directly to prepare a wide range of organozinc compounds, e.g. zinc dialkyl, zinc dialkenyl, zinc dialkynyl, zinc diaryl, zinc diheteroaryl, zinc alkylaryl, zinc alkenylaryl, zinc alkynylaryl, zinc alkylalkenyl, zinc alkylalkynyl, zinc alkenylalkynyl, zinc heteroarylalkenyl, zinc heteroarylalkynyl, zinc heteroarylalkyl, zinc alkyl halide, zinc alkenyl halide, zinc alkynyl halide, zinc heteroaryl halide, zinc aryl halide, zinc dihydride, alkylzinc hydride, alkenylzinc hydride, alkynylzinc hydride, arylzinc hydride, zinc dialkylalkoxide, zinc diarylalkoxide, zinc diheteroarylalkoxide, zinc dialkenylalkoxide, zinc dialkynylalkoxide, alkylzinc alkylalkoxide, alkylzinc arylalkoxide, arylzinc alkylalkoxide, arylzinc arylalkoxide, zinc dialkylamide, zinc diarylamide, alkyl-zinc alkylamide, alkylzinc arylamide, arylzinc alkylamide and arylzinc arylamide compounds. These organozinc compounds can be used to prepare a large number of substances, some of which are highly functionalized, such as pharmaceuticals, natural substance derivatives, polymer materials, agrochemicals, specialities and catalysts.

In particular, the form of zinc according to the invention makes it possible directly to prepare zinc aryl, zinc heteroaryl, zinc alkyl, zinc alkenyl and zinc alkynyl bromides and/or iodides.

The Table below gives an overview of organozinc compounds prepared via an oxidative addition of a form of zinc prepared by the Rieke® process onto organic halides (R. D. Rieke et al., J. Chem. Soc. Chem. Commun. 1973, 269; R. D. Rieke et al., Tetrahedron 1997, 1925; R. D. Rieke et al., J. Org. Chem. 1996, 61, 2726; L. Zhu et al., J. Org. Chem. 1991, 56, 1445). It enables the reactivity of Rieke® zinc to be compared with that of the form of zinc according to the invention.

TABLE 2

Selected syntheses of organozinc compounds via oxidative addition with Rieke ® zinc

| Alkyl/aryl halide | Time [h] | Temp. [° C.] | Product of reaction with zinc | Yield [%] |
|---|---|---|---|---|
| primary | | | | |
| 1-bromobutane | 3 | 90 | n-butylzinc bromide | 97 |
| 1-bromo-6-chlorohexane | 4 | 25 | 6-chlorohexylzinc bromide | 100 |
| secondary | | | | |
| cyclohexyl bromide | 2 | 65 | cyclohexylzinc bromide | 99 |
| sec-butyl bromide | 2.5 | 65 | sec-butylzinc bromide | 95 |
| tertiary | | | | |
| tert-butyl bromide | 1 | 25 | tert-butylzinc bromide | 75 |
| aryl halides | | | | |
| p-bromobenzonitrile | 3 | 65 | 1-bromozinc-4-benzonitrile | 90 |
| ethyl p-bromobenzoate | 2 | 65 | ethyl 1-bromozinc-4-benzoate | 100 |

The form of zinc according to the invention is obtained as follows according to the invention:

Variant 1:

In one embodiment according to the invention for the preparation of the form of zinc according to the invention, Variant 1, technical-grade zinc metal is mixed with one or more compounds of formula I given below. The form of zinc according to the invention, containing the highly reactive zinc metal, is formed in this preparative mixture.

An aprotic organic solvent or solvent mixture is preferably also added to the preparative mixture to give a suspension. Preferably, the added solvent or solvent mixture is that in which the reaction of the form of zinc according to the invention is to take place.

Preferably, according to the invention, the preparative mixture or suspension is stirred at temperatures between −20° C. and 200° C., preferably between 15° C. and 150° C., until activation occurs. The stirring and/or grinding time is preferably between one minute and 5 hours.

Formula I

Compounds of formula I are neutral or basic inorganic or organic compounds of the general composition $X_k Y_l Z_m M_n$, in which:

M is selected from cations of groups 1, 2, 12 or 13 of the periodic table of the elements, preferably from the cations of the metals lithium, sodium, potassium, magnesium, calcium or aluminium;

the anions X, Y and Z independently of one another are selected from the anions of H, halogen, OR, $OSiR_3$, $NR_2$, $N(SiR_3)_2$, SR, $SO_4$, $HSO_4$, $PO_4$, $HPO_4$, $H_2PO_4$, $CO_3$, $NO_3$, $NO_2$, CN, acetate and R;

preferred anions for cations of group 1 of the periodic table being those of OR, $OSiR_3$, $NR_2$, $N(SiR_3)_2$, SR, $PO_4$, $CO_3$ and R, especially those of OR, $NR_2$, $N(SiR_3)_2$, $CO_3$ and R;

preferred anions for cations of groups 2 and 12 of the periodic table being those of halogens, OR, $OSiR_3$, $NR_2$, $N(SiR_3)_2$, $CO_3$ and R, especially those of OR, $NR_2$, $N(SiR_3)_2$, $CO_3$ and R;

preferred anions for cations of group 3 of the periodic table being those of halogens, OR and R;

R independently of one another being selected in all cases from saturated, unsaturated, branched, unbranched, functionalized, non-functionalized, aliphatic, cyclic, heterocyclic or aromatic organic fragments;

preference being afforded to saturated, unsaturated, branched, unbranched, functionalized, non-functionalized, aliphatic, cyclic, heterocyclic or aromatic organic fragments having 1 to 40 carbon atoms, especially 1 to 10 carbon atoms;

the organic fragment preferably being that which appears in the organozinc compound after reactions of zinc with organic halides to give organozinc halides;

the following definitions applying for metals of group 1 of the periodic table of the elements: k=l=0, m=1 and n has the appropriate value for electrical neutrality of the compounds of formula I;

the following definitions applying for metals of groups 2 and 12 of the periodic table of the elements: k=l=1, m=0 and n has the appropriate value for electrical neutrality of the compounds of formula I; and the following definitions applying for metals of group 3 of the periodic table of the elements: k=l=m=1 and n has the appropriate value for electrical neutrality of the compounds of formula I.

Preferred compounds of formula I are alkali-metal alcoholates and alkaline-earth metal alcoholates of the cations lithium, sodium, potassium and magnesium with the anions MeO, EtO, n-PrO, iso-PrO, n-BuO, sec-BuO, iso-BuO, tert-BuO and amylate (AmO), and alkali-metal amides and alkaline-earth-metal amides of the cations lithium, sodium, potassium and magnesium with the anions $N(SiMe_3)_2$, $NMe_2$, $NEt_2$, $N(i-Pr)_2$, $N(n-Pr)_2$ and $NH_2$.

Particular preference is afforded to Li(t-BuO), Na(t-BuO), K(t-BuO), Li(OAm), Na(OAm), K(OAm), Li(i-PrO), Na(i-PrO) and K(i-PrO).

The form of zinc according to the invention, either isolated or in the preparative mixture or suspension, can be used directly for the preparation of organometallic compounds.

Variant 2:

In another embodiment according to the invention for the preparation of the form of zinc according to the invention, Variant 2, one or more transition metals and/or one or more transition-metal compounds are also added to the preparative mixture or suspension according to Variant 1. The form of zinc according to the invention, containing the highly reactive zinc metal, forms in this preparative mixture or suspension.

An aprotic organic solvent or solvent mixture is preferably also added to the preparative mixture to give a suspension. Preferably, the added solvent or solvent mixture is that in which the reaction of the form of zinc according to the invention is to take place.

Preferably, according to the invention, the preparative mixture or suspension is stirred at temperatures between −20° C. and 200° C., preferably between 15° C. and 150° C., until activation occurs. The stirring and/or grinding time is preferably between one minute and 5 hours.

It is preferable according to the invention to add a transition metal or a transition-metal compound and particularly preferable to add a transition-metal compound to the preparative mixture or suspension.

Preferred transition metals according to the invention are iron, cobalt, nickel and copper.

Preferred transition-metal compounds according to the invention are those whose cations can be reduced by zinc in the reaction medium in question, particular preference being afforded to transition-metal salts, salt-like compounds or metal complexes with suitable ligands.

Ligands which can be used according to the invention, independently of one another, are amines, amides, alcohols, alcoholates, ethers, phosphines, thiols, CO, nitrites or organic compounds, e.g. butadiene.

Particularly preferred transition-metal compounds are those of the elements iron, cobalt, nickel and copper.

Very particularly preferred transition-metal compounds are iron halides, cobalt halides, nickel halides and/or copper halides, especially iron(II) chloride, iron(III) chloride, iron(II) bromide, iron(III) bromide, iron(II) iodide, iron(III) iodide, copper(I) chloride, copper(II) chloride, copper(I) bromide, copper(II) bromide, copper(I) iodide and copper(II) iodide, or mixtures of these salts or classes of salts.

The form of zinc according to the invention, either isolated or in the preparative mixture or suspension, can be used directly for the preparation of organometallic compounds.

Variant 3:

In another preferred embodiment according to the invention for the preparation of the form of zinc according to the invention, Variant 3, one or more compounds of formula II are added to the preparative mixture or suspension according to Variant 1 or 2. Preferably, compounds of formula II are added in solution in an aprotic organic solvent or solvent mixture, especially in the solvent or solvent mixture in which the reaction of the highly reactive zinc is to take place. The form of zinc according to the invention, containing the highly reactive zinc metal, forms in this preparative mixture or suspension.

An aprotic organic solvent or solvent mixture is preferably also added to the preparative mixture to give a suspension. Preferably, the added solvent or solvent mixture is that in which the reaction of the form of zinc according to the invention is to take place.

Preferably, according to the invention, the preparative mixture or suspension is stirred at temperatures between −20° C. and 200° C., preferably between 15° C. and 150° C., until activation occurs. The stirring and/or grinding time is preferably between one minute and 5 hours.

$$AZnB \quad \text{Formula II}$$

Compounds of formula II are compounds of the general composition AZnB, in which:
A and B independently of one another are selected from H, halogen, $OR$, $OSiR_3$, $NR_2$, $N(SiR_3)_2$, $CO_3$, $CN$, acetate and R, preferably from halogen, $OR$, $NR_2$ and R;
R independently of one another being selected in all cases from saturated, unsaturated, branched, unbranched, functionalized, non-functionalized, aliphatic, cyclic, heterocyclic or aromatic organic fragments;
preference being afforded to saturated, unsaturated, branched, unbranched, functionalized, non-functionalized, aliphatic, cyclic, heterocyclic or aromatic organic fragments having 1 to 40 carbon atoms, especially 1 to 10 carbon atoms;
the organic fragment preferably being that which appears in the organozinc compound after reactions of zinc with organic halides to give organozinc halides.

Preferably, according to the invention, the preparative mixture or suspension is stirred at temperatures between −20° C. and 200° C., preferably between 15° C. and 150° C., until activation occurs. The stirring and/or grinding time is preferably between one minute and 5 hours.

The form of zinc according to the invention, either isolated or in the preparative mixture or suspension, can be used directly for the preparation of organometallic compounds.

Variant 4:

In another embodiment according to the invention for the preparation of the form of zinc according to the invention, Variant 4, another reagent or reagent mixture is added to the preparative mixture or suspension according to Variant 1, 2 or 3 for additional activation of the form of zinc according to the invention. The preparative mixture or suspension is stirred and/or ground for between one minute and 5 hours at between −78° C. and the boiling point of the preparative mixture or suspension, preferably at between 0° C. and 50° C. The form of zinc according to the invention, containing the highly reactive zinc metal, forms in this preparative mixture or suspension.

This additional reagent or reagent mixture is preferably selected from 1,2-dibromoethane, iodine, organic and/or inorganic acids, organic and/or inorganic halogenosilanes or mixtures of these reagents.

The form of zinc according to the invention, either isolated or in the preparative mixture or suspension, can be used directly for the preparation of organometallic compounds.

Variant 5:

In another embodiment according to the invention for the preparation of the form of zinc according to the invention, Variant 5, a suspension of technical-grade zinc metal in an aprotic organic solvent or solvent mixture is pretreated by the addition of a reagent or reagent mixture and stirred for between one minute and 5 hours at between −78° C. and the boiling point of the suspension, preferably at between 0° C. and 50° C.

This reagent or reagent mixture is preferably selected from 1,2-dibromoethane, iodine, organic and/or inorganic acids, organic and/or inorganic halogenosilanes or mixtures of these reagents.

After this pretreatment of the zinc metal, the form of zinc according to the invention is prepared according to Variant 1, 2, 3 or 4. The form of zinc according to the invention, containing the highly reactive zinc metal, forms in this preparative mixture or suspension.

The form of zinc according to the invention, either isolated or in the preparative mixture or suspension, can be used directly for the preparation of organometallic compounds.

In Variants 1 to 5 the molar ratio of technical-grade zinc used to compound of formula I is preferably 1:1 to 1:0.0001, particularly preferably 1:0.1 to 1:0.0001.

In Variants 2 to 5 the molar ratio of technical-grade zinc used to transition metals or transition-metal compounds is preferably 1:0.5 to 1:0.0001, particularly preferably 1:0.1 to 1:0.0001.

In Variants 3 to 5 the molar ratio of technical-grade zinc used to components of formula II is preferably 1:10 to 1:0.0001, particularly preferably 1:1 to 1:0.0001.

In Variants 4 and 5 the additional reagent or reagent mixture is preferably as follows:
- organic acid:acetic acid or trifluoroacetic acid, or mixtures thereof;
- inorganic acid:hydrochloric acid;
- inorganic halogenosilane:tetrachlorosilane;
- organic halogenosilane:trimethylchlorosilane, dimethyldichlorosilane or methyltrichlorosilane, or mixtures thereof.

In Variants 4 and 5 a total of 0.1 to 20 mol %, preferably 1 to 10 mol % and particularly preferably 1 to 5 mol % of reagent or reagent mixture is used, based on the amount of zinc.

As well as the substances which can be added, according to the invention, to the mixtures according to Variants 1 to 5, one or more other reagents and/or auxiliary substances can be added to the preparative mixture or suspension. For example, the reactivity of the form of zinc according to the invention obtained according to Variants 1 to 5 can be further increased by the additional use of common methods of metal activation.

In all the variants described above, the preparative mixture or suspension is preferably stirred and/or ground in the absence of air and moisture. The reaction mixtures according to the invention can also be subjected to an ultrasound treatment.

Preferred aprotic organic solvents for all the variants described above are aliphatic or aromatic hydrocarbons, heterocycles, ethers, amines, nitriles, amides or mixtures thereof.

The term 'aliphatic hydrocarbons' includes cyclic, saturated, unsaturated, branched and unbranched hydro-carbons. The term 'ethers' includes cyclic, saturated, unsaturated, branched, unbranched, identically substituted and differently substituted ethers having at least one oxygen atom, preferably one to four oxygen atoms. The term 'amines and amides' includes cyclic, aliphatic, saturated, unsaturated, branched, unbranched, identically substituted and differently substituted amines and amides having at least one nitrogen atom, preferably one to four nitrogen atoms. The term 'aromatic hydrocarbons' includes unsubstituted, monosubstituted and polysubstituted aromatic compounds. The term 'heterocycles' includes substituted, unsubstituted, aromatic, saturated and unsaturated cyclic compounds whose ring consists of at least four carbon atoms and at least one atom from the group comprising oxygen, sulfur and nitrogen heteroatoms, preferably four to six carbon atoms and one to three heteroatoms.

Preferred solvents are hexane, heptane, methylcyclohexane, cycloheptane, methylcycloheptane and isomers thereof; benzene, toluene, cumene, ethylbenzene, xylenes and isomers thereof; pyridine; dimethyl ether, diethyl ether, methyl tert-butyl ether, di-n-butyl ether, THF, 2-methyl-THF and cyclopentyl methyl ether; and dimethoxyethane, diethoxymethane, diethoxyethane and polyethylene glycol.

In all the variants described above, the form of zinc according to the invention can be separated from the other components of the preparative mixture or suspension by suitable processes. Suitable processes are those comprising one or more steps selected from sieving, filtration, decantation, centrifugation, distillation at normal pressure, distillation at reduced pressure, drying and total evaporation. Other common processes for isolating solids can likewise be used. The form of zinc according to the invention which has been separated off can again be used directly for the preparation of organo-metallic compounds.

In all the variants described above, the form of zinc according to the invention can be stored, preferably at between −100° C. and 200° C. and particularly preferably in the range between 0° C. and 50° C. It is preferably stored in the absence of air and moisture and particularly preferably under vacuum or in an inert gas atmosphere, e.g. a nitrogen or argon atmosphere. It is preferable to avoid exposure to air or protic compounds such as water. Even after storage, the preparative mixture or suspension containing the highly reactive zinc metal can be used directly for the preparation of organometallic compounds.

The invention is illustrated in greater detail by the Examples below, without thereby implying a limitation.

The experiments described below were carried out in the absence of air and moisture in an argon atmosphere. The solvents and substrates used were of technical grade.

EXAMPLE 1

Preparation of the Form of Zinc According to the Invention According to Variant 1 Using Compounds of Formula I 10.0 g of commercially available zinc powder (<125 µm) and 1 mol % of sodium tert-butoxide are weighed into a reactor. After the addition of 10 g of a solvent as shown in Table 3, the suspension obtained is stirred for one hour at the boiling point (or alternatively for ten hours at 20° C.).

EXAMPLE 2

Preparation of the Form of Zinc According to the Invention According to Variant 2 Using Compounds of Formula I and Transition-Metal Compounds a) 10.0 g of commercially available zinc powder (<125 µm), 1 mol % of sodium tert-butoxide and 1 mol % of copper(I) iodide are weighed into a reactor. After the addition of 10 g of a solvent as shown in Table 3, the suspension obtained is stirred for one hour at the boiling point (or alternatively for ten hours at 20° C.).

b) 10.0 g of commercially available zinc powder, 0.5 mol % of magnesium ethoxide and 0.5 mol % of iron(III) chloride are weighed into a reactor. After the addition of 10 g of a solvent as shown in Table 3, the suspension obtained is stirred for one hour at the boiling point (or alternatively for ten hours at 20° C.).

c) 10.0 g of commercially available zinc powder (<325 µm), 1 mol % of lithium bistrimethylsilylamide and 0.5 mol % of nickel(II) iodide are weighed into a reactor. After the addition of 10 g of a solvent as shown in Table 3, the suspension obtained is stirred for one hour at the boiling point (or alternatively for ten hours at 20° C.).

EXAMPLE 3

Isolation of the Form of Zinc According to the Invention

The form of zinc according to the invention prepared according to Example 2a is filtered off, dried under vacuum and stored under an inert gas atmosphere.

Comparative Examples

EXAMPLE 4

Activation of Zinc Metal with 1,2-dibromoethane and Trimethylsilyl Chloride 10.0 g of commercially available zinc powder (<325 μm) are suspended in approx. 10 g of THF. 5 mol % of 1,2-dibromo-ethane are added to this suspension, which is refluxed for approx. 30 minutes. After cooling to room temperature, 2 mol % of trimethylsilyl chloride are added and the reaction mixture is refluxed again for approx. 30 minutes.

EXAMPLE 5

Activation of Zinc Metal with Transition-Metal Compounds 10.0 g of commercially available zinc powder (<125 μm) and 1 mol % of copper(I) iodide are weighed into a reactor. After the addition of 10 g of a solvent as shown in Table 3, the suspension obtained is stirred for one hour at the boiling point.

EXAMPLE 6

Activation of Zinc Metal with Compounds of Formula II and Transition-Metal Compounds (But Without Compounds of Formula I)

10.0 g of commercially available zinc powder, 1 mol % of copper(I) iodide and 10 mol % of a solution of n-butylzinc bromide in a solvent as shown in Table 3 are weighed into a reactor. The suspension obtained is stirred for one hour at the boiling point.

Reactions with n-butyl bromide:

EXAMPLE 7

1.0 equivalent of n-butyl bromide is added to 1.2 equivalents of the form of zinc according to the invention prepared according to Example 1, and the reaction mixture is stirred at the temperature indicated in the Table. After the reaction time indicated in Table 3, the conversion is determined by GC analysis.

EXAMPLES 8 TO 10

1.0 equivalent of n-butyl bromide is added to 1.2 equivalents of the form of zinc according to the invention prepared according to Examples 2a to 2c, and the reaction mixture is stirred at the temperature indicated in the Table. After the reaction time indicated in Table 3, the conversion is determined by GC analysis.

EXAMPLES 11 TO 13

Additional Use of Compounds of Formula II

Approx. 10 mol % of a solution of n-butylzinc bromide in a solvent as shown in Table 3, and then 1.0 equivalent of n-butyl bromide, are added to 1.2 equivalents of the form of zinc according to the invention prepared according to Examples 2a to 2c, and the reaction mixture is stirred at the temperature indicated in the Table. After the reaction time indicated in Table 3, the conversion is determined by GC analysis.

EXAMPLE 14

Approx. 10 mol % of a solution of n-butylzinc bromide in a solvent as shown in Table 3, and then 1.0 equivalent of n-butyl bromide, are added to 1.2 equivalents of the form of zinc according to the invention prepared according to Example 3, in 10 g of a solvent as shown in Table 3, and the reaction mixture is stirred at the temperature indicated in the Table. After the reaction time indicated in Table 3, the conversion is determined by GC analysis.

EXAMPLES 15 TO 17

Comparative Examples (Comp.)

1.0 equivalent of n-butyl bromide is added to 1.2 equivalents of zinc metal treated according to Examples 4 to 6, and the reaction mixture is stirred at the temperature indicated in the Table. After the reaction time indicated in Table 3, the conversion is determined by GC analysis.

The results of the reactions of Examples 7 to 17 can be found in the Table below. Both the conversion and the identity of the product were verified by methods of GC/MS analysis after the derivatization of a reaction aliquot with iodine and sodium thiosulfate solution according to:

TABLE 3

$$\text{n-BuZnBr} \xrightarrow[\text{2. Na}_2\text{S}_2\text{O}_3]{\text{1. I}_2/\text{Ether}} \text{n-BuI} + \text{"ZnBrI"}$$

Results of the reactions with n-butyl bromide

| Example | Metal activation according to Example | Temperature [°C.] | Solvent | Reaction time [h] | Conversion [%] |
|---|---|---|---|---|---|
| 7 | 1 | 80 | methylcyclohexane | 4.5 | 59 |
| 8 | 2a | 80 | methylcyclohexane | 5.0 | 95 |
| 9 | 2b | 80 | toluene | 5.5 | 97 |
| 10 | 2c | 60 | THF | 4.5 | 98 |

TABLE 3-continued $$\text{n-BuZnBr} \xrightarrow[\text{2. Na}_2\text{S}_2\text{O}_3]{\text{1. I}_2/\text{Ether}} \text{n-BuI} + \text{"ZnBrI"}$$

Results of the reactions with n-butyl bromide

| Example | Metal activation according to Example | Temperature [° C.] | Solvent | Reaction time [h] | Conversion [%] |
|---|---|---|---|---|---|
| 11 | 2a | 80 | methylcyclohexane | 3.0 | 100* |
| 12 | 2b | 80 | toluene | 4.0 | 93 |
| 13 | 2c | 60 | THF | 3.0 | 96 |
| 14 | 3 | 80 | methylcyclohexane | 3.0 | 100* |
| 15 (Comp.) | 4 | 65 | THF | 20.0 | 15 |
| 16 (Comp.) | 5 | 80 | methylcyclohexane | 6.5 | 10 |
| 17 (Comp.) | 6 | 80 | methylcyclohexane | 4.0 | 62 |

*100% means that only product is found and n-butyl bromide is no longer detectable.

Other Examples according to the invention are given below:

EXAMPLE 18

Preparation of N-Butylzinc Bromide, Isolated Yield and Composition of the Product Solution a) Preparation of the Form of Zinc According to the Invention:

30.12 g (460.69 mmol) of commercially available zinc, 0.44 g (4.58 mmol) of sodium tert-butoxide and 0.89 g (4.67 mmol) of Cu(I)I are suspended in 9.15 g of methylcyclohexane (unconditioned) and stirred for approx. 2 hours at 70° C. After the zinc metal has settled out, the brown supernatant solution is siphoned off and the metal is washed with twice 10 g of methylcyclohexane and dried under vacuum.

b) Preparation of n-butylzinc Bromide:

10.85 g (165.95 mmol) of the form of zinc according to the invention previously prepared in 18a are suspended in approx. 15 g of methylcyclohexane in a 250 ml Schlenck flask fitted with a reflux condenser and an internal temperature sensor. Approx. 50% of the total amount of n-BuZnBr solution previously prepared according to Examples 12 and/or 15 (total amount: 4.95 g, 17.5 mmol; 71 wt. % in toluene) is added via a dropping funnel. The remaining 50% of n-BuZnBr is mixed with 19.39 g (141.5 mmol) of n-BuBr in the dropping funnel and the clear solution is added to the reaction mixture. The suspension is then heated by means of a heating mantle at 100° C. for 90 minutes and kept at 100° C. for 30 minutes. After cooling to room temperature, approx. 20 g of methylcyclohexane are added and the mixture is filtered through a D3 frit to give a clear solution. The composition of the product solution is examined by wet analysis to give the values below. The isolated yield, based on n-BuBr used, is 98%.

TABLE 4

| Analytical values | | | | |
|---|---|---|---|---|
| OH$^-$ | Br$^-$ | Zn$^{2+}$ | Conc. | Yield |
| mmol/g | | | wt. % | % |
| 2.33 | 2.33 | 2.34 | 47.2 | 98[1] |

[1] added amount of n-BuZnBr taken into account, washing solution taken into account

EXAMPLE 19

Reaction with Isopropyl Bromide 10.10 g (154.5 mmol) of highly reactive zinc metal prepared according to Example 18a are suspended in approx. 10 g of methylcyclohexane. 15.9 g (129.4 mmol) of isopropyl bromide in approx. 14 g of methylcyclohexane are then added and the mixture is stirred for three hours at 60° C. to 70° C. It is then filtered to give a clear solution and a sample is analysed. The residue is washed with THF and the washing filtrate is analysed separately. The identity of the product was confirmed by GC/MS; iso-PrBr was no longer detectable. The isolated yield (including washing filtrate) is 84.1%, based on iso-PrBr used.

TABLE 5

| | Analytical values | | | | |
|---|---|---|---|---|---|
| Sample | OH$^-$ | Br$^-$ | Zn$^{2+}$ | Conc. | Yield |
| | mmol/g | | | wt. % | % |
| Initial solution | 2.36 | 2.35 | 2.35 | 44.5 | 80.2 |
| Washing solution | 0.31 | 0.31 | 0.32 | 5.8 | 3.9 |

EXAMPLE 20

Preparation of ethyl 4-bromozincbutanoate 34.28 g (525 mmol) of technical-grade zinc metal, 2.04 g (10.7 mmol) of Cu(I)I and 1.10 g (11.4 mmol) of sodium tert-butoxide are suspended in 21.85 g of toluene and stirred at 100° C. for one hour. After cooling to 40° C., 65.7 g of THF and 3.03 g (27.9 mmol) of trimethylchlorosilane are added. After stirring for 20 minutes, the reaction suspension is heated to 60° C. and 48.2 g (247.1 mmol) of ethyl 4-bromobutanoate are metered in over three hours. When the metered addition is complete, a sample is taken and examined by wet analysis; the result is shown in Table 6. Stirring is then continued for 3 hours at 60° C. After cooling to room temperature, the suspension is filtered to give a clear solution and analysed. The residue is washed with THF. An aliquot of the product solution is hydrolysed with water and examined by GC/MS analysis. The identity of the product is confirmed. The yield is 94.9%.

TABLE 6

| | Analytical values for Example 20: | | | | |
|---|---|---|---|---|---|
| Sample | $OH^-$ | $Br^-$ mmol/g | $Zn^{2+}$ | Conc. wt. % | Yield % |
| after end of metered addition | 1.29 | 1.30 | 1.31 | | |
| after filtration | 1.58 | 1.62 | 1.61 | 41.1 | 88.6 |
| washing solution | 0.46 | 0.46 | 0.47 | | 6.3 |

The total base was determined by acidimetry, the bromide content by argentometry and the $Zn^{2+}$ by complexometry.

The invention claimed is:

1. A process for the preparation of a form of zinc comprising reacting zinc metal with a neutral or basic inorganic or organic compound of formula I $$X_k Y_l Z_m M_n$$

wherein

M is a cation of groups 1, 2, 12 or 13 of the periodic table of the elements,

X, Y and Z are independently selected from H, halogen, OR, $OSiR_3$, $NR_2$, $N(SiR_3)_2$, SR, $SO_4$, $HSO_4$, $PO_4$, $HPO_4$, $H_2PO_4$, $CO_3$, $NO_3$, $NO_2$, CN, acetate and R;

R is a saturated, unsaturated, branched, unbranched, functionalized, non-functionalized, aliphatic, cyclic, heterocyclic or aromatic organic fragment;

wherein if M is a metal of group 1 of the periodic table of the elements: k=l=0, m=1 and n has the appropriate value for electrical neutrality of the compound of formula I;

wherein if M is a metal of groups 2 and 12 of the periodic table of the elements: k=l=1, m=0 and n has the appropriate value for electrical neutrality of the compound of formula I; and wherein if M is a metal of group 13 of the periodic table of the elements: k=l=m=1 and n has the appropriate value for electrical neutrality of the compound of formula I;

wherein the compound of formula I is an alkali-metal alcoholate or alkaline-earth metal alcoholates of the cations lithium, sodium, potassium or magnesium with an anion of formula MeO, EtO, n-PrO, iso-PrO, n-BuO, sec-BuO, iso-BuO, tert-BuO or and AmO, or an alkali-metal amide or an alkaline-earth metal amide of the cations lithium, sodium, potassium or and magnesium with the anions N(SiMe3)2, NMe2, NEt2, N(i Pr)2, N(n-Pr)2 and NH2, or a mixture thereof.

2. The process according to claim 1, wherein the following are used as compounds of formula I: Li(t-BuO), Na(t-BuO), K(t-BuO), Li(OAm), Na(OAm), K(OAm), Li(i-PrO), Na(i-PrO) and K(i-PrO), or mixtures thereof.

3. The process according to claim 1, wherein one or more transition metals or one or more transition-metal compounds are added to the preparative mixture.

4. The process according to claim 1, wherein the cation is selected from iron, cobalt, nickel, copper, or mixtures thereof.

5. The process according to claim 1, wherein the transition-metal compounds are selected from compounds or mixtures of compounds whose cations can be reduced by zinc in the reaction medium in question.

6. The process according to claim 1, wherein the transition-metal compounds are transition-metal salts, salt-like compounds or metal complexes with suitable ligands, or mixtures of these compounds, the ligands independently of one another being selected from amines, amides, alcohols, alcoholates, ethers, phosphines, thiols, CO, nitriles or organic compounds like butadiene.

7. The process according to claim 1, wherein the cation is selected from iron, cobalt, nickel or copper.

8. The process according to claim 1, wherein the transition-metal compounds are transition metal compounds of the elements iron halides, cobalt halides, nickel halides and/or copper halides and particularly preferably iron(II) chloride, iron (III) chloride, iron(II) bromide, iron(III) bromide, iron(II) iodide, iron(III) iodide, copper (I) chloride, copper (II), chloride, copper (I) bromide, copper(II) bromide, copper(I) iodide, copper (II) iodide or mixtures of these transition-metal compounds or salts.

9. The process according to claim 1, wherein one or more compounds of the composition AZnB (formula II) are added to the preparative mixture, wherein: A and B independently selected from H, halogen, OR, OSiR3, NR2, N(SiR3)2, C03, CN, acetate and R wherein R is defined above;

R is selected from saturated, unsaturated, branched, unbranched, functionalized, nonfunctionalized, aliphatic, cyclic, heterocyclic or aromatic organic fragments.

10. The process according to claim 1, wherein an aprotic organic solvent or solvent mixture is added to the preparative mixture.

11. The process according to claim 1, wherein thepreparative mixture or suspension is stirred and/or ground.

12. The process according to claim 1, wherein the preparative mixture or suspension is stirred and/or ground at temperatures between −20° C. and 200° C.

13. The process according claim 1, wherein the preparative mixture or suspension is stirred and/or ground for between one minute and 5 hours.

14. The process according to claim 1, wherein the preparative mixture or suspension is stirred and/or ground for 1 to 20 hours, at room temperature.

15. The process according to claim 1, wherein for additional activation of the form of zinc according to the invention, another reagent or reagent mixture, selected from 1,2-dibromoethane, iodine, organic and/or inorganic acids, organic and/or inorganic halogenosilanes or mixtures of these reagents, is added to the preparative mixture or suspension.

16. The process according to claim 1, wherein the reagent or reagent mixture is selected from the following compounds or mixtures thereof: acetic acid or trifluoroacetic acid, or mixtures thereof; hydrochloric acid; tetrachlorosilane; and trimethylchlorosilane, dimethyldichlorosilane or methyltrichlorosilane, or mixtures thereof.

17. The process according to at claim 1, wherein a total of 0.5 to 20 mol % of reagent or reagent mixtures used, based on the amount of zinc used.

18. The process according to claim 1, wherein the aprotic organic solvent used are aliphatic or aromatic hydrocarbons, heterocycles, ethers, amines, nitriles, amides or mixtures thereof.

19. The process according to claim 1, wherein the preparative mixture or suspension containing the form of zinc according to the invention is treated with ultrasound.

20. The process according to claim 1, wherein the preparative mixture or suspension is stored in the absence of air and moisture.

21. The process according to claim 1, wherein the preparative mixture or suspension is Used directly to prepare an organometallic compound.

22. The process according to claim 1, wherein the zinc is separated from the other components of the preparative mixture or suspension.

23. A form of zinc prepared by the process of claim 1, wherein the highly reactive zinc metal has a particle size above 2 microns.

24. A form of zinc according to claim 23, wherein it is not contaminated with alkali-metal halides, cyanides, sulfates, nitrates, nitrites and/or acetates.

25. A form of zinc according to claim 24, wherein in oxidative addition reactions with n-butyl bromide, it produces yields of n-butylzinc bromide of over 50% within a period of five hours at temperatures below 150° C.

26. A form of zinc according to claim 24, wherein in oxidative addition reactions with n-butyl bromide, produces yields of n-butylzinc bromide greater than or equal to 60%.

* * * * *